(12) United States Patent
Nordström et al.

(10) Patent No.: US 10,301,775 B2
(45) Date of Patent: May 28, 2019

(54) METHOD FOR PRODUCING A FOAM WEB

(71) Applicant: Stora Enso OYJ, Helsinki (FI)

(72) Inventors: Jan-Erik Nordström, Nacka (SE); Jari Räsänen, Imatra (FI)

(73) Assignee: Stora Enso OYJ, Helsinki (FI)

( * ) Notice: Subject to any disclaimer, the term of this patent is extended or adjusted under 35 U.S.C. 154(b) by 0 days.

(21) Appl. No.: 15/516,278

(22) PCT Filed: Sep. 30, 2015

(86) PCT No.: PCT/IB2015/057477
§ 371 (c)(1),
(2) Date: Mar. 31, 2017

(87) PCT Pub. No.: WO2016/051350
PCT Pub. Date: Apr. 7, 2016

(65) Prior Publication Data
US 2017/0306561 A1    Oct. 26, 2017

(30) Foreign Application Priority Data

Oct. 3, 2014    (SE) ........................ 1451172

(51) Int. Cl.
*D21F 11/00*    (2006.01)
*A61L 2/08*    (2006.01)
(Continued)

(52) U.S. Cl.
CPC ............ *D21F 11/002* (2013.01); *A61L 2/087* (2013.01); *D21F 5/002* (2013.01); *D21F 5/022* (2013.01);
(Continued)

(58) Field of Classification Search
CPC .......... D21F 11/002; D21F 9/003; D21F 1/02; D21F 5/002; D21F 5/022; D21H 21/56;
(Continued)

(56) References Cited

U.S. PATENT DOCUMENTS 1,740,280 A    12/1929    Bryant
2,999,788 A *   9/1961    Winthrop .................. D01D 5/04
                                                    162/146

(Continued)

FOREIGN PATENT DOCUMENTS

CA    2466576 A1 *    5/2003    ............ D21F 11/002
CA    2962711 A1 *    4/2016    ............ D21F 11/002
(Continued)

OTHER PUBLICATIONS

International Search Report for PCT/IB2015/057477, dated Jan. 11, 2016.
Written Opinion for PCT/IB2015/057477, dated Jan. 11, 2016.

*Primary Examiner* — Jose A Fortuna

(57) ABSTRACT

Method for producing a sterilized foam web, wherein the method comprising the steps of preparing a wet foam (1), feeding the wet foam (1) to a head box (2, 11), distributing the wet foam by the head box (2, 11), treating the wet foam (1) with electron beam radiation (3a, 3b, 3c) to immobilize and sterilize the wet foam (1), receiving the electron beam treated foam on a moving wire (4) to form a foam web (6, 13), pressing and the foam web (6, 13), and drying the foam web (6, 13).

10 Claims, 1 Drawing Sheet

(51) Int. Cl.
  *H01J 37/317* (2006.01)
  *D21F 5/00* (2006.01)
  *D21F 5/02* (2006.01)
  *D21H 27/30* (2006.01)

(52) U.S. Cl.
  CPC ........... *D21H 27/30* (2013.01); *H01J 37/317* (2013.01); *H01J 2237/316* (2013.01)

(58) Field of Classification Search
  CPC .. D21H 27/30; H01J 2237/316; H01J 37/317; A61L 2/087; Y10S 68/90
  See application file for complete search history.

(56) References Cited

U.S. PATENT DOCUMENTS

| | | | | |
|---|---|---|---|---|
| 3,007,840 | A * | 11/1961 | Wilcox | D21F 11/002 162/101 |
| 3,494,824 | A | 2/1970 | Roberts | |
| 3,716,449 | A * | 2/1973 | Gatward | D21F 11/002 162/101 |
| 3,837,999 | A * | 9/1974 | Chung | D21F 9/003 162/101 |
| 3,871,952 | A * | 3/1975 | Robertson | D21F 11/002 162/101 |
| 4,285,767 | A * | 8/1981 | Page | D21F 1/02 162/216 |
| 4,443,297 | A * | 4/1984 | Cheshire | D21F 11/002 162/101 |
| 4,543,156 | A * | 9/1985 | Cheshire | D21F 11/002 162/101 |
| 4,686,006 | A * | 8/1987 | Cheshire | D21F 1/02 162/101 |
| 4,767,793 | A | 8/1988 | Schisler et al. | |
| 5,164,045 | A * | 11/1992 | Awofeso | D21F 9/006 162/101 |
| 5,480,717 | A | 1/1996 | Kundel | |
| 5,506,035 | A * | 4/1996 | Van Phan | A61L 15/24 428/196 |
| 5,720,851 | A * | 2/1998 | Reiner | D21F 11/002 162/101 |
| 5,904,809 | A * | 5/1999 | Rokman | D21F 11/002 162/101 |
| 6,136,153 | A * | 10/2000 | Rokman | D21F 9/003 162/101 |
| 6,238,518 | B1 * | 5/2001 | Rokman | D21F 9/003 162/101 |
| 6,261,679 | B1 * | 7/2001 | Chen | A61F 13/53 264/45.2 |
| 6,500,302 | B2 * | 12/2002 | Dwiggins | D21F 11/002 162/101 |
| 6,531,078 | B2 * | 3/2003 | Laine | D21F 11/002 264/122 |
| 6,603,054 | B2 * | 8/2003 | Chen | A61F 13/53 210/508 |
| 6,835,418 | B2 * | 12/2004 | Capizzi | B05B 7/025 427/243 |
| 7,285,183 | B2 * | 10/2007 | Kajander | B32B 13/14 162/135 |
| 7,416,636 | B2 * | 8/2008 | Blomqvist | D21F 11/002 162/101 |
| 7,462,259 | B2 * | 12/2008 | Kajander | B32B 13/14 162/135 |
| 8,268,737 | B1 | 9/2012 | Kumar | |
| 2001/0024716 | A1 * | 9/2001 | Chen | A61F 13/53 428/317.9 |
| 2002/0066544 | A1 * | 6/2002 | Dwiggins | D21F 11/002 162/101 |
| 2002/0088581 | A1 * | 7/2002 | Graef | D21F 11/002 162/158 |
| 2003/0193836 | A1 * | 10/2003 | Kinsley, Jr. | B01F 3/04453 366/307 |
| 2003/0220039 | A1 * | 11/2003 | Chen | A61F 13/53 442/327 |
| 2003/0232135 | A1 * | 12/2003 | Capizzi | B05B 7/0037 427/244 |
| 2004/0112558 | A1 * | 6/2004 | Garnier | D21H 13/10 162/129 |
| 2005/0039870 | A1 * | 2/2005 | Blomqvist | D21F 11/002 162/101 |
| 2006/0283565 | A1 * | 12/2006 | Kajander | B32B 13/14 162/101 |
| 2008/0004369 | A1 | 1/2008 | Seppala | |
| 2015/0083354 | A1 * | 3/2015 | Strandqvist | D04H 1/498 162/146 |
| 2017/0306561 | A1 * | 10/2017 | Nordstrom | D21F 11/002 |

FOREIGN PATENT DOCUMENTS

| | | | | |
|---|---|---|---|---|
| DE | 3307736 A | | 9/1984 | |
| DE | 19857096 | | 7/1999 | |
| DE | 19917809 A1 * | | 11/1999 | ............ D21F 1/02 |
| EP | 1232875 A1 | | 8/2002 | |
| EP | 1449869 A1 | | 8/2004 | |
| GB | 1329409 A * | | 9/1973 | ............ D21F 11/002 |
| WO | WO-9602702 A1 * | | 2/1996 | ............ D21F 11/002 |
| WO | 0243784 A2 | | 6/2002 | |
| WO | WO-03040469 A1 * | | 5/2003 | ............ D21F 11/002 |
| WO | 2004050752 A1 | | 6/2004 | |
| WO | WO-2016051350 A1 * | | 4/2016 | ............ D21F 11/002 |

* cited by examiner

METHOD FOR PRODUCING A FOAM WEB

This application is a U.S. National Stage under 35 U.S.C. § 371 of International Application No. PCT/IB2015/057477, filed Sep. 30, 2015, which claims priority to Swedish patent application No. 1451172-9 filed Oct. 3, 2014.

The present invention relates to a method for producing a sterilized foam web.

The invention further relates to a sterilized foam web.

Finally, the invention relates to a foam product.

Today there are known methods to produce various webs of foams in a paper machine by letting wet foam pass through a headbox to a moving wire and then dry the foam web, such as DE19857096, U.S. Pat. No. 5,571,1383, DE19917809, U.S. Pat. Nos. 4,686,006 and 4,285,767.

However, it is not easy to dry the foam web with the use of conventional, paper machine, drying equipment's, such as IR or hot roll contact drying, without collapsing, or densifying, the foam layer. Moreover, the wet foam tends to collapse already when the wet foam hits the wire.

An object with the present invention is to provide a new method for producing a foam web, in a paper machine, which eliminates, or alleviates, at least some of the above mentioned drawbacks. Yet another object is to provide a foam web, which comprises one or several layers, by using a headbox which allows a 3D-foam web with a high bulk to be obtained.

In the following description of the invention the term "natural fibres" will be used. In this context the term comprises wood fibres, botanical fibres, and/or their derivate or their mixtures.

Moreover, the term "foam" or "wet foam" will be frequently used. The wet foam comprises a mixture of natural fibres, liquid and at least one additive. At least one of the additives is suitable to be stabilized/stiffened by electron beam radiation (see below). The liquid of the foam may be water or blends of water with various volatile solvents. Moreover, the liquid may be a totally solvent based liquid, such as methanol, ethanol, toluene etc.

The description further involves the term "sterilized foam web". In this context the term comprises a flat or 3D-formed foam web made from wet foam. The foam web is suitably used to manufacture foam products, such as food containers, trays, cups, gas filters, air filters, liquid filters, mouth covers, insulations, sanitary pads and tampons etc. However, these are just examples and it is obvious that other foam products made from the inventive foam web are possible.

Moreover, the description comprises the term "electron beam radiation". Electron beam radiation is a process which involves the use of electrons, usually of high energy, to treat an object for a variety of purposes. Possible uses for electron radiation include sterilization and to cross-link polymers. Electron energies typically vary from the keV to MeV range, depending on the depth of penetration required. The radiation dose is usually measured in Gray (Gy).

The inventive method is characterized in that the method comprising the steps of:
preparing a wet foam,
feeding the wet foam to a head box,
distributing the wet foam by the head box,
treating the wet foam with electron beam radiation to immobilize and sterilize the wet foam,
receiving the electron beam treated foam on a moving wire to form a foam web,
pressing and the foam web, and
drying the foam web.

The sterilized foam web is characterized in that the web is obtained by the above mentioned method.

The foam product is characterized in that it is at least partly manufactured from the above foam web.

In the following, the invention will be described further with reference to the drawings, wherein.

Figure 1:
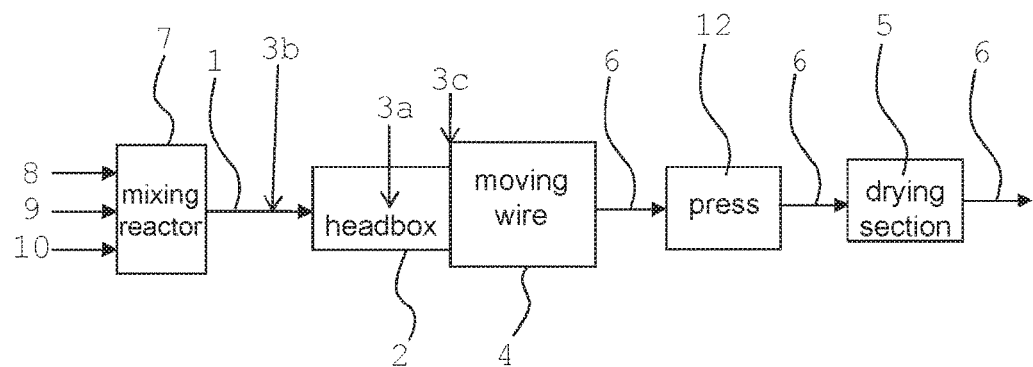
FIG. 1 shows a schematic illustration of an apparatus arrangement in a paper machine for forming a single-layer of a sterilized foam web.

The apparatus arrangement in FIG. 1 comprises a mixing reactor 7 for mixing wet foam 1. The arrangement further comprises a forming section 2, 3a, 3b, 3c, 4, 5, 12 to form a sterilized foam web 6, 13 from the wet foam 1.

The mixing reactor 7 comprises feeding means 8, 9, 10 to add natural fibres 8, liquid 9 and additives 10 to the mixing reactor 7. The reactor comprises mixing means (not shown in FIG. 1) for mixing the natural fibres 8, liquid 9 and additives 10 to form the wet foam 1. The wet foam 1 is then transported to a headbox 2, 11.

The headbox 2, 11 uniformly distributes the wet foam 1 on to a moving wire 4, such that, a foam web 6, 13 is formed on the moving wire 4. On the wire 4 the foam becomes dewatered/densified. The wire 4 may be a single wire 4, or a twin-wire 4 where the foam is located between the twin-wire 4. The wire 4 section may involve a suction box in order to densify the foam further.

Figure 2:
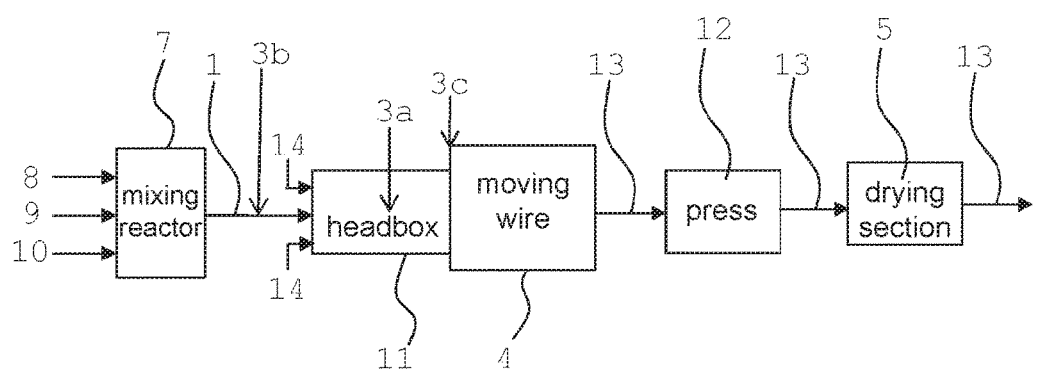
FIG. 2 shows a schematic illustration of an apparatus arrangement in a paper machine for forming a multi-layer of a sterilized foam web.

The headbox 2 may be a single-layer headbox 2, FIG. 1, or a multi-layer headbox 11, FIG. 2. A single-layer headbox 2 distributes a single-layer foam web 6 on to the moving wire 4, wherein the foam web 6 comprising the wet foam 1. A multi-layer headbox 11 distributes a multi-layer foam web 13 on the moving wire 4, wherein at least one of the layers comprising the wet foam 1. The other layers in the multi-layer web may origin from foam suspension 14 with the same composition as the wet foam 1 or a foam suspension 14 with another composition with other properties than the wet foam 1. The other layers may also origin from a non-foam suspension, such as, for example a fibre suspension 14 comprising natural fibres and liquid, or other suspensions 14 comprising synthetic or unnatural fibres, such as acrylic, polyester, rayon, nylon etc.

The multi-layer headbox 11 in FIG. 2 comprising a setup for manufacturing a multi-layer foam web with three layers, wherein at least one of the layers comprising a foam layer. However, it is obvious that also more than three layers are possible and of course also a multi-layer comprising two layers.

Before, and/or at the moment and/or after the wet foam 1 hits the wire 4, the wet foam 1 is subjected to electron beam radiation 3a, 3b, 3c. The electron beam radiation immobilizes and sterilizes the wet foam 1, such that, the wet foam 1 becomes more stable and prevent that the wet foam 1 collapse when it hits the wire 4 and forms the foam web 6, 13. This will give a stable/stiff and sterilized foam web 6, 13 with a high bulk or well defined structure.

In a first embodiment, the electron beam radiation treatment 3a subjected to the wet foam is located in the headbox 2, 11.

In a second embodiment, the electron beam radiation treatment 3b subjected to the wet foam is located before the headbox 2, 11.

In a third embodiment, the electron beam radiation treatment 3c subjected to the wet foam is located after the headbox 2, 11.

The electron beam radiation is adjusted to a certain level, such that, the generated electrons will pass and create the foam into the needed stiffness and structure prior drying. By using various web speeds, and adjustments in the headbox 2, 11 (solids content, chemicals, gas amount), various properties and thicknesses of foam can be created and to be stiffened using electron beam equipment. By using various crosslinking additives and various amounts of electron beam radiation it is possible to create various types of properties in the foam web from soft rubber-like to hard brittle structures for various applications, e.g. fibre structures that can carry load in high humidity conditions. Also materials with various absorption and adsorption properties may be created i.e. induce e.g. hydrophobic and/or hydrophilic properties for various amphoteric materials and combinations with chosen polymers.

The electron beam treated foam web 6, 13 is transported by the wire 4 to the pressing section 12. The pressing section 12 comprises at least one press 12, which presses liquid out of the foam web 6, 13. The pressed web 6, 13 is then transported to the drying section 5 for drying the foam web. The drying section 5 may comprise a hot drying cylinder 5, an IR (infra-red) heater 5, and/or hot air blowing dryers 5.

The invention may create various foam web types fast and accurately consisting of various components and containing natural minerals and even, if needed, un-organic materials to provide new types of materials into needed packaging (soft/hard lightweight material to carry various products during transport and sales) and building needs, such as insulation, soundproofing, heat/fire retardant materials etc.

Moreover, by choosing suitable electron beam radiation level it is possible to harden the surface of the foam, whereas deeper in to the material a compressible spring-like material is achieved.

Electron beam radiation is not harmful to the working environment because it can be directed accurately and the amount that is passing the material can be caught through a roller or a collector-box located beneath the electron beam.

A major benefit with the invention is that all mixture of wet foam 1 which comprises natural fibres 8, liquid 9 and additives 10 (also electron beamable activators) are prepared in the mixing reactor just before the wet foam is distributed through the headbox. Hence, the wet foam has a very short lifetime. This means that all the wet foam is used in the production of the foam web. The main principle is fast foam, fast use and simultaneously fast fixing of the wet foam by electron beam treatment to form the 3D-structured foam. This allows that no returning to the circulations is needed, since all wet foam is used. The fast fixing of the foam will ensure a high speed production of the foam web.

So when the short lifetime wet foam is formed and fed out from the headbox, the flexibility of foam will be immediately locked as it is by using electron beam radiation. The electron beam radiation acts with the electron beam radiation active compounds and results in a rigid network of fibres.

This rigidly of the structure may be adjusted by using different energy levels of electronic beam radiation. Hence, it is possible to achieve foam webs from flexible to hard rigid network. The foam web is immediately available to continue in to converting process to a foam product.

In the foregoing, the invention has been described on the basis of some specific embodiments. It is appreciated, however, that other embodiments and variants are possible within the scope of the following claims. For example the electron beam radiation treatment may be located before the headbox, at the headbox, after the headbox or a combination of these mentioned.

The invention claimed is:

1. Method for producing a sterilized foam web, comprising the steps of:
   preparing a wet foam in a mixing reactor, wherein the wet foam comprises a mixture of natural fibers, liquid and at least one foam stabilizing additive curable by electron beam radiation;
   feeding the wet foam to a head box;
   distributing the wet foam by the head box;
   treating the wet foam with electron beam radiation to immobilize and sterilize the wet foam after the mixing reactor and before the wet foam hits a moving wire;
   receiving the electron beam treated foam on the moving wire to form a foam web;
   pressing the foam web, and
   drying the foam web.

2. Method according to claim 1, wherein the electron beam radiation is subjected to the wet foam at the headbox.

3. Method according to claim 1, wherein the electron beam radiation is subjected to the wet foam before the headbox.

4. Method according to claim 1, wherein the electron beam radiation is subjected to the wet foam after the headbox.

5. Method according to claim 1, wherein the headbox is a single-layer headbox, and the headbox distributes the wet foam to form a single-layer foam web on the moving wire.

6. Method according to claim 1, wherein the headbox is a multi-layer headbox, and the headbox distributes the wet foam and at least one further suspension to form a multi-layer foam web on the moving wire.

7. Method according to claim 1, wherein the drying comprising a hot cylinder for drying the foam web.

8. Method according to claim 1, wherein the drying comprises IR radiation for drying the foam web.

9. Method for producing a sterilized foam web, comprising the steps of:
   preparing a wet foam in a mixing reactor, wherein the wet foam comprises a mixture of natural fibers, liquid and at least one foam stabilizing additive curable by electron beam radiation;
   feeding the wet foam to a head box;
   distributing the wet foam by the head box;
   treating the wet foam with electron beam radiation to immobilize and sterilize the wet foam after the headbox and before the wet foam hits a moving wire;
   receiving the electron beam treated foam on the moving wire to form a foam web;
   pressing the foam web, and
   drying the foam web.

10. Method for producing a sterilized foam web, comprising the steps of:
    preparing a wet foam in a mixing reactor, wherein the wet foam comprises a mixture of natural fibers, liquid and at least one foam stabilizing additive curable by electron beam radiation;
    feeding the wet foam to a head box;
    distributing the wet foam by the head box;
    treating the wet foam with electron beam radiation to immobilize and sterilize the wet foam at the headbox and before the wet foam hits a moving wire;
    receiving the electron beam treated foam on the moving wire to form a foam web;
    pressing the foam web, and
    drying the foam web.

* * * * *